United States Patent
Graf et al.

(10) Patent No.: US 8,882,737 B2
(45) Date of Patent: Nov. 11, 2014

(54) CONTAINER FILLED WITH A LIQUID CONCENTRATE FOR MAKING DIALYSATE

(75) Inventors: Thomas Graf, Bad Homburg (DE); Paul Gastauer, Tassin la Demi Lune (FR); Philippe Laffay, Stainte Foy les Lyon (FR); Francois Dumont D'Ayot, Lyons (FR); Pascal Lengrand, Saint Genis Leval (FR); Bertrand Thibault, Saint Laurent du Var (FR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 13/570,124

(22) Filed: Aug. 8, 2012

(65) Prior Publication Data

US 2013/0071048 A1  Mar. 21, 2013

Related U.S. Application Data

(63) Continuation of application No. 12/227,897, filed as application No. PCT/EP2007/004879 on Jun. 1, 2007, now Pat. No. 8,251,971.

(30) Foreign Application Priority Data

Jun. 2, 2006 (EP) .................................... 06011472

(51) Int. Cl.
*A61B 19/00* (2006.01)
*A61J 1/10* (2006.01)
(Continued)

(52) U.S. Cl.
CPC ................ *A61J 1/10* (2013.01); *Y10S 383/903* (2013.01); *B65D 31/005* (2013.01);
(Continued)

(58) Field of Classification Search
CPC .... B65D 75/008; B65D 31/005; B65D 31/04; B65D 31/08; B65D 31/10; B65D 31/16; B65D 33/00; B65D 33/02; B65D 75/5855; Y10S 383/00; Y10S 383/903; Y10S 383/906; Y10S 383/907; Y10S 604/905; B31B 2237/05; B31B 2237/50; B31B 2221/40; B31B 2221/50; B31B 2237/20; B31B 2237/25; B31B 2237/40; B31B 2237/403; B31B 2237/406; B31B 2219/23; B31B 2221/20; B31B 2221/25; A61J 1/10; A61J 2001/00; A61J 1/12; A61M 1/1656; A61M 2001/1668; A61M 2001/167
USPC .......... 604/408, 403, 410, 415, 416; 383/210, 383/38, 103, 104, 107, 118, 119, 120, 121, 383/122, 123, 124, 125, 126

See application file for complete search history.

(56) References Cited

U.S. PATENT DOCUMENTS 3,405,859 A * 10/1968 Phillips, Jr. .................... 229/108
3,935,993 A * 2/1976 Doyen et al. .................... 383/94
(Continued)

FOREIGN PATENT DOCUMENTS

CN 1077691 10/1993
CN 2440015 7/2001
(Continued)

*Primary Examiner* — Adam Marcetich
(74) *Attorney, Agent, or Firm* — Jacobson Holman Hershkovitz, PLLC.

(57) ABSTRACT

A self standing bag having two side wall sheets and a bottom sheet. To flatten the bag, the bottom sheet is sandwiched between the two side wall sheets and symmetrically folded along a line parallel to its bottom edge, separating the bag into a four-layer part and a two-layer part. In the two-layer part, the bag includes first sloped sealing lines extending between a first two points on the top edges of the side wall sheets and spaced from the vertical side wall edges by a first distance, to a second two points spaced from the vertical edges of the side wall sheets by a second distance less than the first distance. The four-layer part includes second sloped sealing lines extending between the second two points and a third two points on the bottom edges of the side wall sheets.

25 Claims, 7 Drawing Sheets

(51) Int. Cl.
   *A61M 1/16*     (2006.01)
   *B65D 75/00*    (2006.01)
   *A61M 5/32*         (2006.01)
   *B65D 30/16*        (2006.01)
   *B65D 33/00*        (2006.01)
   *B65D 65/26*        (2006.01)
   *B65D 30/22*        (2006.01)
   *B65D 30/00*        (2006.01)
   *B65D 33/02*        (2006.01)
   *B65D 30/10*        (2006.01)

(52) U.S. Cl.
   CPC .......... *B31B 2219/23* (2013.01); *Y10S 383/907* (2013.01); *B31B 2237/50* (2013.01); *B31B 2221/20* (2013.01); *B31B 2221/50* (2013.01); *A61M 1/1656* (2013.01); *B65D 75/008* (2013.01); *B65D 33/00* (2013.01); *A61M 1/1668* (2014.02)
   USPC .......... 604/408; 604/410; 604/415; 604/416; 383/104; 383/210; 383/38; 383/107; 383/119; 383/121; 383/123; 383/903; 383/907

(56) References Cited

U.S. PATENT DOCUMENTS

| | | | | |
|---|---|---|---|---|
| 4,361,235 | A * | 11/1982 | Gautier | 206/527 |
| 4,810,109 | A * | 3/1989 | Castel | 383/105 |
| 4,837,849 | A * | 6/1989 | Erickson et al. | 383/104 |
| 4,978,025 | A | 12/1990 | Fougeres | |
| 5,350,240 | A * | 9/1994 | Billman et al. | 383/104 |
| 5,352,043 | A * | 10/1994 | Takagaki et al. | 383/104 |
| 5,356,069 | A * | 10/1994 | Bochet et al. | 229/104 |
| 5,401,546 | A | 3/1995 | Meattle | |
| 5,928,554 | A | 7/1999 | Olson et al. | |
| 6,092,933 | A * | 7/2000 | Treu | 383/104 |
| 6,224,528 | B1 | 5/2001 | Bell | |
| 6,322,044 | B1 * | 11/2001 | Vangedal-Nielsen | 249/61 |
| 6,461,043 | B1 * | 10/2002 | Healy et al. | 383/204 |
| 7,018,099 | B2 | 3/2006 | Caudle | |
| 7,055,720 | B1 * | 6/2006 | Pritchard | 222/107 |
| 7,306,095 | B1 | 12/2007 | Bourque et al. | |
| 8,251,971 | B2 * | 8/2012 | Graf et al. | 604/408 |
| 2002/0076471 | A1 | 6/2002 | Olsson | |
| 2002/0094922 | A1 * | 7/2002 | Edwards et al. | 493/221 |
| 2002/0118895 | A1 | 8/2002 | Watabe | |
| 2002/0141664 | A1 | 10/2002 | Matsuda et al. | |
| 2002/0147091 | A1 * | 10/2002 | Healy et al. | 493/213 |
| 2003/0059128 | A1 * | 3/2003 | Vangedal-Nielsen | 383/4 |
| 2003/0059130 | A1 | 3/2003 | Yoneyama et al. | |
| 2003/0168120 | A1 | 9/2003 | Brehm et al. | |
| 2005/0031230 | A1 | 2/2005 | Ernst et al. | |
| 2005/0147329 | A1 | 7/2005 | Arvizu | |
| 2005/0167363 | A1 | 8/2005 | Taylor | |
| 2005/0173455 | A1 * | 8/2005 | Hagihara | 222/107 |
| 2006/0108375 | A1 * | 5/2006 | Pritchard | 222/107 |
| 2006/0120631 | A1 | 6/2006 | Tang | |
| 2006/0186045 | A1 * | 8/2006 | Jensen et al. | 210/645 |

FOREIGN PATENT DOCUMENTS

| | | |
|---|---|---|
| DE | 8607304 | 8/1986 |
| EP | 02379730 | 9/1987 |
| EP | 0264044 | 4/1988 |
| EP | 0368757 | 5/1990 |
| EP | 0515745 | 12/1992 |
| EP | 1 277 667 | 1/2003 |
| FR | 2749763 | 12/1997 |

\* cited by examiner

| Part of the bag | reference in figures | preferred length/mm | most preferred length/mm |
| --- | --- | --- | --- |
| horizontal edges of sheets | 2a, 2b, 3a, 3b, 4a, 4b | 300-450 | 375 |
| vertical edges of side sheets | 2c, 2d, 3c, 3d | 200-380 | 290 |
| vertical edges of bottom sheet | 4c, 4d | 180-240 | 210 |
| first recess of first points A', A" | a | 50-100 | 75 |
| second recess of second points B', B" | b | 0-30 | 15 |
| third recess of third points C1', C2', C1", C2" | c | 50-100 | 75 |
| fourth recess of fourth points D1', D2', D1", D2" | d | 40-70 | 55 |
| fifth recess of fifth points E1', E2', E1", E2" | e | 55-85 | 70 |

Fig. 6

CONTAINER FILLED WITH A LIQUID CONCENTRATE FOR MAKING DIALYSATE

This is a continuation application of application Ser. No. 12/227,897 filed on Dec. 2, 2008 now U.S. Pat. No. 8,251,971, which is a national stage of PCT/EP07/0004879 filed Jun. 1, 2007 and published in English, which has a priority of European no. 06011472.5 filed Jun. 2, 2006, hereby incorporated by reference, and hereby claims the priority thereof.

BACKGROUND OF THE INVENTION

1. Field of the Invention

The invention relates to the field of containers for providing liquid concentrates for making ready-to-use dialysis fluid for a dialysis treatment of a patient by an artificial kidney.

2. Description of the Related Art

In case of kidney failure the functions of the human kidneys have to be substituted by an artificial kidney device. Wide spread therapies comprise peritoneal dialysis and hemodialysis. In peritoneal dialysis, dialysis fluid is conducted via special implanted catheters to the peritoneal cavity of a patient and regularly exchanged with fresh fluid, thus purifying the human blood by diffusion of substances to be removed and by extracting excess water by osmotic pressure gradients through the peritoneum of the patient.

In hemodialysis the blood of a patient is circulated in an extracorporeal blood circuit for several hours. The blood passes the blood chamber of a dialyser where a semipermeable membrane, most commonly in the shape of thousands of hollow fibres, separates a blood chamber from a dialysate chamber that is part of a dialysate circuit. The blood is purified from substances to be removed by diffusion through the membrane as such substances are 20 usually not contained in the dialysate flowing into the dialysate chamber. Other substances that are to be retained in the blood at least in certain concentrations and that can also pass the membranes like electrolytes are contained in the fresh dialysate in physiological concentrations. By applying a pressure gradient excess water can be transferred from the blood to the dialysate chamber and then be removed together with the dialysate exciting the dialysate chamber.

Most contemporary hemodialysis devices prepare the dialysate required for the hemodialysis treatment during the treatment from concentrates and water in a single-pass system, i.e. the prepared dialysate only passes the dialyser once and is discarded thereafter. Depending on the type of dialysate to be used one or two concentrates are required. In the case of bicarbonate dialysis that currently represents the most common dialysis mode two concentrates are necessary because of chemical incompatibilities of some of the substances. The first or "A"-component usually consists of an acidic part that also contains most of the required electrolytes. The second or "B"-component consists mainly of sodium bicarbonate in this case. Whereas the second component can also be delivered in dry powder form, the first component is still widely distributed as a fluid in rigid containers if no central concentrate supply system exists where the concentrate is prepared at a central location and then distributed to the treatment places via a piping network.

Typical dilution ratios of the A-component with water are about 1+33, 1+34 or 1+44, the B-component contributing further shares between 1 to 2 parts of liquid. Common dialysate flow rates for a hemodialysis treatment are of the order of 500 ml/min. Taking a four hour treatment a liquid volume of about 120 liters has to be circulated through the dialysate chamber requiring concentrate volumes of at least 3 to 4 liters each. To enable a variation of concentration ratios and also to provide a certain tolerance to prolong a treatment and to compensate the waste of dialysate in certain conditions of a hemodialysis device when for security reasons the continuously prepared dialysate is short-circuited to the drain, usual containers for liquid dialysate concentrates contain 5 or more liters of liquid concentrate.

The dialysate prepared by diluting the concentrates with water on-line during a treatment of a patient may also be used as substitution liquid in the case of a hemofiltration or hemodiafiltration treatment. Today many treatment devices also provide for such on-line substitution modes leading to an even higher demand of liquid concentrates.

Up to now the fluid concentrates have usually been delivered in rigid plastic containers as the weight of the concentrate requires a certain stability of the container. Such containers also simplify the shipping of large lots as they can easily be arranged in layers on top of each other.

These rigid containers have the disadvantage that because of their rigidity they are comparatively expensive as the container walls have to be thick enough leading to higher material expenses. Furthermore, the empty containers are bulky making the further processing cumbersome. The large amount of material to be recycled or discarded adds further to the cost.

It is an object of the present invention to provide a container with liquid dialysate that requires less material in the manufacturing process but still provides sufficient stability to the filled container even when being filled with three liters of liquid and more and during the use of the container when the container is gradually emptied.

The problem of the invention is solved by a container filled with a liquid dialysate for making dialysate for a dialysis treatment, characterised in that the container is a self-standing bag made of flexible elastomeric sheets.

The invention is based on the observation that in other technical fields self-standing bags made of flexible elastomeric sheets are in wide-spread use. Such bags require much less material for their production and much less space when being empty. However, there appeared to be the prejudice in the field of dialysis that such bags are not suitable for the manufacture of containers for liquid concentrates for dialysis. In fact the weight of several kilogramms of liquid is large for a flexible bag bearing the risk that a bag may crack during use or not rest in a stable position to allow the extraction of the concentrate through the suction pipe of the hemodialysis device during a treatment procedure.

In the framework of this patent application a self-standing bag is understood to be a bag having its barycentre well defined above its bottom standing area when being filled with a medium so that the filled bag rests in a stable standing orientation on its own.

The inventors of the present invention observed that this prejudice can in fact be overcome and that it is possible to produce self-standing bags made of flexible elastomeric sheets filled with liquid dialysate concentrate having a volume of three liters and even more.

In a preferred embodiment this bag is made from two elastomeric flexible side wall sheets having rectangular shape with horizontal top and bottom and two vertical edges, and one elastomeric flexible bottom wall sheet also having rectangular shape with two horizontal and two vertical edges. When being empty this bag may be put into a flat configuration where the bottom wall sheet is sandwiched between the two elastomeric side wall sheets and wherein the bottom wall sheet is symmetrically single-folded parallel to its horizontal edges and the horizontal edges of the bottom wall sheet coincide with the horizontal bottom edges of the two side wall sheets. In the flat configuration the empty bag is thus divided into a lateral four-layer part in the lower part of the bag and a lateral two-layer part in the upper part of the bag.

A connector part can conveniently be sandwiched between the two horizontal top edges of the side wall sheets wherein the two horizontal top edges and the connector part are joined in a fluid tight way by a seal, preferably a welding line.

In further embodiments of the invention several parts of the bag are jointly sealed, preferably by welding: the vertical edges of the side wall sheets in the lateral two-layer part, the vertical edges of the bottom wall sheet with the neighbouring parts of the side wall sheets, and the horizontal edges of the bottom wall sheet with the neighbouring horizontal bottom edges of the side wall sheets.

A preferred embodiment of the bag comprises first sloped sealing lines on each side of the bag joining the side wall sheets in the lateral two-layer part between first points on the horizontal top edges of the side wall sheets that are recessed from the outer ends of the horizontal edges, in other words, the first points on the horizontal top edges of the side wall sheets are spaced from the vertical edges of the side wall sheets, and second points that are along or spaced from the vertical edges of the side wall sheets and that are positioned on the line separating the lateral two-layer part from the lateral four-layer part. Second sloped sealing lines join each side wall sheet and the neighbouring bottom wall sheet in the lateral four-layer part on each side of the bag between third points on the horizontal bottom edges that are recessed from the outer ends of the horizontal edges, in other words, the third points are spaced from the vertical edges of the side wall sheets, and the second points.

The second points may be recessed from the vertical edges of the side wall sheets and the bag may comprise further horizontal sealing lines between the second points and the neighbouring vertical edges of the side wall sheets along the line separating the two-layer part from the four-layer part thus joining all four layers along these horizontal sealing lines.

In a particularly stable embodiment of the self-standing bag there are third sloped sealing lines on each side of the bag between the third points and fourth points on the vertical edges of both the side wall sheets and the bottom wall sheet in the four-layer part joining only the bottom wall sheet and the neighbouring side wall sheet. Additional fourth sloped sealing lines on each side of the bag between the second and the fourth points joining only the bottom wall sheet and the neighbouring side wall sheet further contribute to the stability of the self-standing bag.

In another embodiment of the invention the first, second and fourth sloped sealing lines, but not the third sloped sealing lines exist. Instead the sheet material of the side wall sheets and the bottom wall sheet in the corner areas below the second sloped sealing lines and below cutting edges leading from the fourth points to fifth points on the second sloped sealing lines is removed. The cutting edges may be reinforced by fifth sloped sealing lines on each side of the bag between the fourth and the fifth points joining only the bottom wall sheet (4) and the neighbouring side wall sheet. In this case a beak-like flap is formed on both sides of the bag that protects the zone around the second points where four sheets of the side wall sheets and the bottom wall sheet are joined.

All sealing lines are preferably created by welding techniques, but generally other joining processes like gluing are also possible. In special cases a sealing line may simply be established by folding a larger sheet along the required line. Such embodiments are hereby explicitly encompassed by using the expression "seal" throughout this document. Furthermore, the sealing lines are preferably straight lines.

In a particularly preferred embodiment of the self-standing bag the sheet material of the bottom wall sheet between the fourth sloped sealing lines and the vertical edges has been removing, preferably by punching. Both side wall sheets can therefore directly be joined in this area thus avoiding welding areas consisting of four layers of elastomeric sheets that could give rise to problems in reliable sealing the outer layers.

The second sloped sealing line may at least partly be a peel seam that is adapted to absorb excessive pressure in the bag. Should high pressure suddenly develop in the bag as in the case of a crash of the bag on a hard floor the peel seam can at least partly open whereby the pressure is diminished in a controlled manner minimising the risk that the bag gets cracks.

With the self-standing bag according to the invention it is possible to provide dialysate liquid concentrates in a bag made of elastomeric flexible sheets with common volumes of 3 to 8 liters, preferably 5 to 6 liters. Such a bag could also be delivered containing just a dry or slurry concentrate that when being diluted with water directly before use produces the same amount of dialysate liquid concentrate that is sufficient for a whole blood treatment of a patient.

For embodiments of the self-standing bag according to the invention where the bag is made from two side wall and one bottom wall sheets a further advantageous embodiment makes use of a layered bottom wall sheet wherein the two outer layers consist of different materials. Using the same material for one outer layer of the bottom wall sheet and the side wall sheets or at least the outer layer of the side wall sheets facing each other further simplifies the manufacture of certain embodiments of the self-standing bag according to the invention as the stability of a bag area where four sheets would have to be joined by welding can be enhanced without the removal of parts of the bottom wall sheet.

BRIEF DESCRIPTION OF THE DRAWINGS

More details and advantages of the invention will become apparent from example embodiments of the container according to the invention as illustrated in a non-limiting manner in the drawings wherein.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
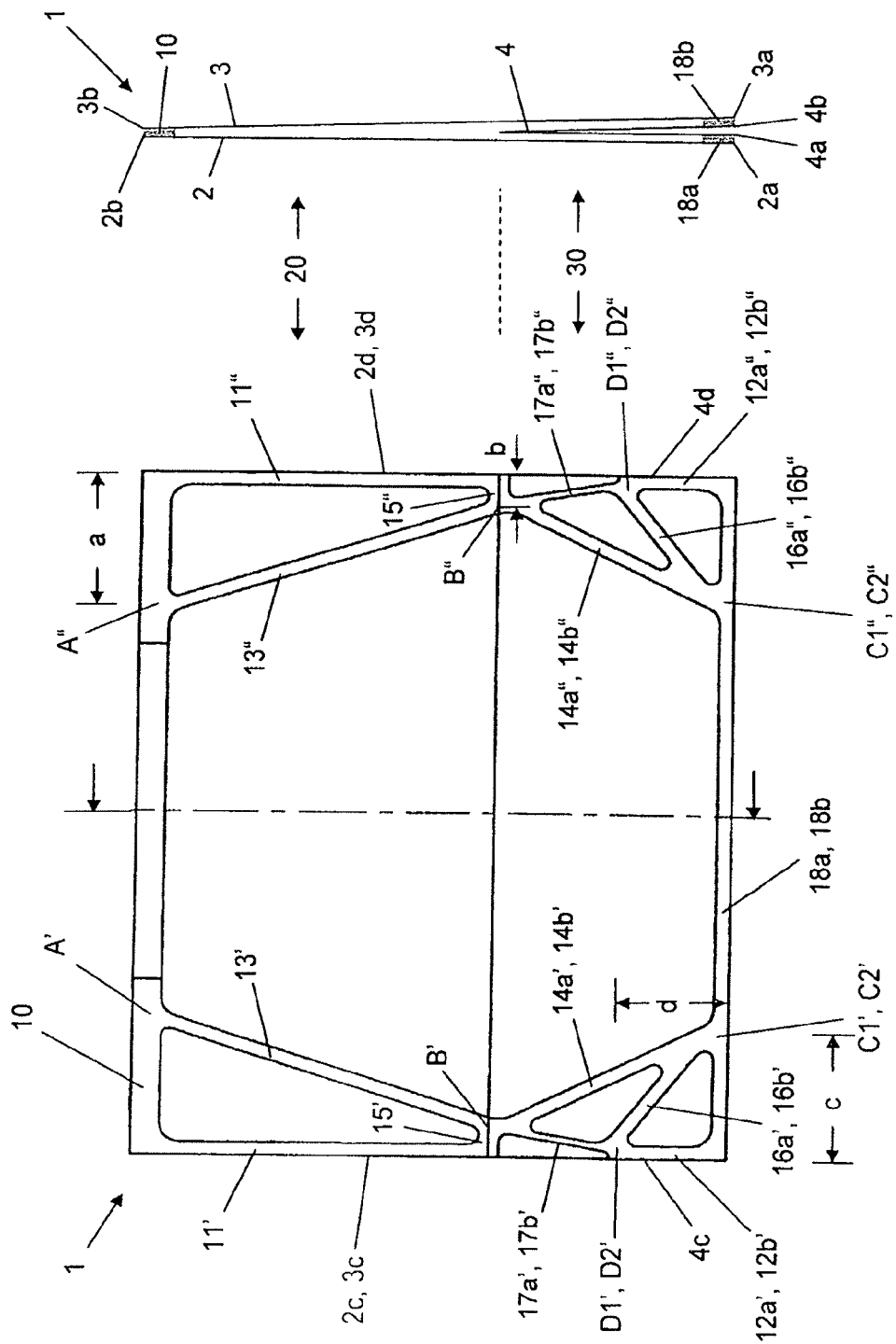
FIG. 1*a* shows a first embodiment of the self-standing bag according to the invention in an empty, flat configuration, FIG. 1*b* a lateral cross-section of the bag as indicated in FIG. 1*a*, FIG. 2 the bag of FIG. 1*a* in a three-dimensional configuration when being filled, FIG. 3 the joining of the bottom and side wall sheets of the bag of FIG. 2, FIG. 4 the bag of FIG. 2 with peel seams to absorb pressure waves, FIG. 5 an alternative embodiment of the bag of FIG. 2 for avoiding any damage in the case of excessive pressure, FIG. 6 a table for preferred geometries of the example embodiments of the bag according to the invention, FIG. 7 a second embodiment of the self-standing bag according to the invention in an empty, flat configuration, FIG. 8 the bag of FIG. 7 in a three-dimensional configuration when being filled, FIG. 9 the joining of the bottom and side wall sheets of the bag of FIG. 8, and FIG. 10 a third embodiment of the self-standing bag according to the invention showing a view similar to FIG. 9 for the second embodiment.

In FIG. 1a a first embodiment of the self-standing bag 1 according to the invention is shown in a flat configuration directly after having been manufactured and before the bag 1 is filled with liquid dialysate concentrate. FIG. 1b presents a lateral cross-section of the bag 1 as indicated in FIG. 1a. The self-standing bag 1 is made from three rectangular sheets of flexible elastomeric material: two similar side wall sheets 2 and and one bottom wall sheet 4. The bottom wall sheet 4 is sandwiched between the side wall sheets 2 and 3 wherein the bottom wall sheet 4 is symmetrically single-folded parallel to its horizontal edges 4a and 4b, and the horizontal edges of the bottom wall sheet coincide with the horizontal bottom edges 2a and 3a of the two side wall sheets 2 and 3. In the flat configuration the empty bag is thus divided into a lateral four-layer part 30 and a lateral two-layer part 20. The vertical edges 2c and 2d of the first side wall sheet and 3c and 3d of the second side wall sheet coincide with each other and with the folded vertical edges 4c and 4d of the bottom wall sheet.

The two horizontal top edges 2b and 3b are joined by a seal 10 wherein a connector part may be sandwiched and sealed between the side wall sheets in a part of the sealing line 10 (not shown in FIGS. 1a and 1b). The vertical edges 2c, 2d and 3c, 3d of the side wall sheets are joined by seals 11' and 11" in the lateral two-layer part 20 (an apostrophe in a reference sign shall denote parts on the left hand side of the bag and a double apostrophe the corresponding symmetric part on the right hand side in this patent document).

The vertical edges 4c and 4d of the bottom wall sheet are joined with the neighbouring parts of the side wall sheets 2 and 3 by further seals 12a', 12b' and 12a", 12b" (for parts that exist in the lateral four-layer part twice the suffix "a" is used in this patent document to denote an item that originates from the first side wall sheet 2 and the bottom wall sheet 4 whereas the suffix "b" is used to denote the corresponding symmetric item that originates from the second side wall sheet 3 and the bottom wall sheet 4). Furthermore the horizontal edges 4a and 4b of the bottom wall sheet are joined with the neighbouring horizontal bottom edges 2a and 3a of the side wall sheets by seals 18a, 18b, thereby providing a sealed volume in the middle of the bag.

As an alternative of making the bag from three separate sheets the side wall sheets 2 and 3 and the bottom wall sheet 4 may be made from a single web wherein the horizontal bottom edges 2a, 3a of the side wall sheets and 4a, 4b of the bottom wall sheet are made by folding the web along the horizontal edges. Such folding lines are considered to be sealing lines in the context of the present invention. It would also be possible to manufacture the bag from a flat tubular film where the folded edges of the tubular film either represent the vertical or the horizontal edges of the side wall sheets. Upon at least partly opining the folded edges (e.g. for inserting a connector at the top or for allowing appropriate forming of the bag) other sealing lines can be realised by folding lines without departing from the concept of the present invention.

The embodiment shown in FIG. 1a further comprises first sloped sealing lines 13', 13" between the side wall sheets 2 and 3 in the lateral two-layer part 20 on each side of the bag between first points A', A" on the horizontal top edges sealing line 10, that are recessed by a first distance a from the ends of the horizontal edges, and second points B', B" that are less or not recessed by a second distance b from the vertical edges 2c, 3c and 2d, 3d, respectively, of the side wall sheets. The second points B', B" are positioned on the line separating the lateral two-layer part 20 from the lateral four-layer part 30.

The self-standing bag 1 also comprises second sloped sealing lines 14a', 14b' and 14a", 14b" joining each side wall sheet 2, 3 and the neighbouring bottom wall sheet 4 in the lateral four-layer part 30 on each side of the bag between third points C 1', C2' and C1", C2" on the horizontal bottom edges 2a, 3a, that are recessed by a third distance c from the ends of the horizontal bottom edges, and the second points B', B". The second distance b is small compared with the first and third distances a and c. In the embodiment shown in FIG. 1a the first and third distances a and c are identical. Along the recesses with the second distance b and hence along the line separating the two-layer part 20 from the four-layer part 30 the bag 1 further comprises horizontal sealing lines 15', 15" between the second points B', B" and the neighbouring vertical edges 2c, 3c and 2d, 3d of the side wall sheets wherein the horizontal sealing lines 15', 15" join all four sheets in this region.

The bag 1 also contains third sloped sealing lines 16a', 16b' and 16a", 16b" on each side of the bag between the third points C1', C2' and C1", C2" and fourth points D1', D2' and D 1", D2" on the vertical edges 2c, 3c and 2d, 3d of both side wall sheets and the vertical edges 4c, 4d of the bottom wall sheet in the four-layer part 30 joining only the bottom wall sheet 4 and the neighbouring side wall sheet 2 or 3. The fourth points D1', D2' and D1", D2" are recessed from the bottom horizontal edges 2a, 3a by fourth distances d.

In addition the self-standing bag 1 comprises fourth sloped sealing lines 17a', 17b' and 17a", 17b" on each side of the bag between the second points B', B" and the fourth points D1', D2' and D1", D2" joining only the bottom wall sheet 4 and the neighbouring side wall sheet 2 or 3.

All sealing lines are preferably produced by welding techniques for which a manifold of processes are available for those skilled in the art. By way of example the welding may be carried out by applying heat directly, using ultrasonic waves or laser irradiation.

Figure 2:
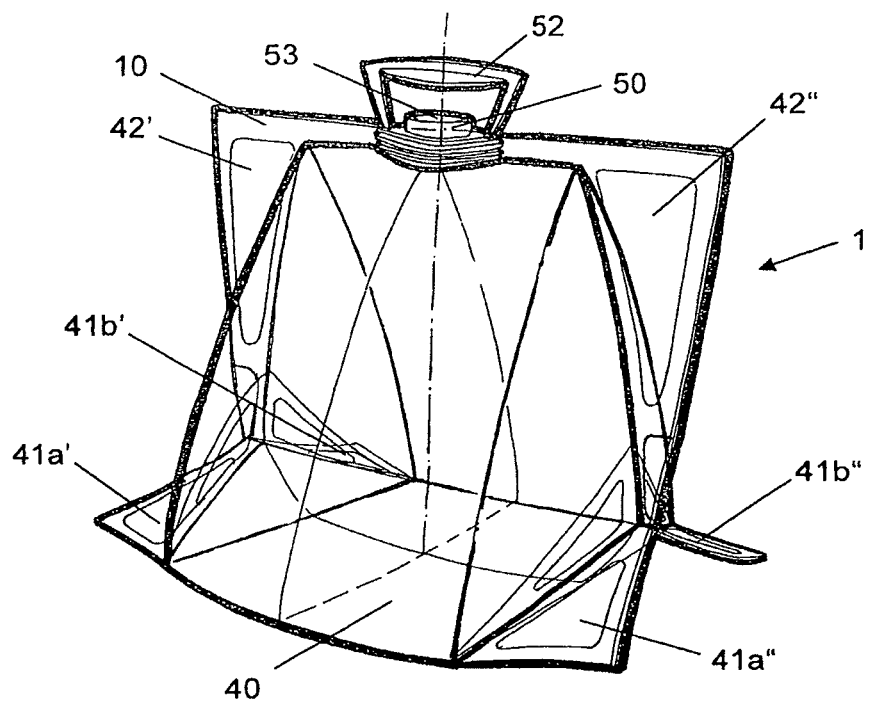

After the bag has been filled with liquid dialysate concentrate it assumes a three-dimensional shape as can be seen in FIG. 2. For reasons of clarity the liquid itself is not depicted in FIG. 2. In this configuration the self-standing bag has a squared bottom plane 40 whereas the interior has a wedge shaped volume with decreasing horizontal cross-section when going from the bottom to the top of the bag 1. This provides for a centre-of-gravity at low height and thus for an improved stability of the bag. The stability is also enhanced horizontally by the bottom side flaps 41a', 41b' and 41a", 41b" and vertically by the top side flaps 42' and 42". Also shown in FIG. 2 is a connector part 50 that is sealed in a sandwiching manner between the side wall sheets 2 and 3 in the sealing line zone 10.

Figure 3:
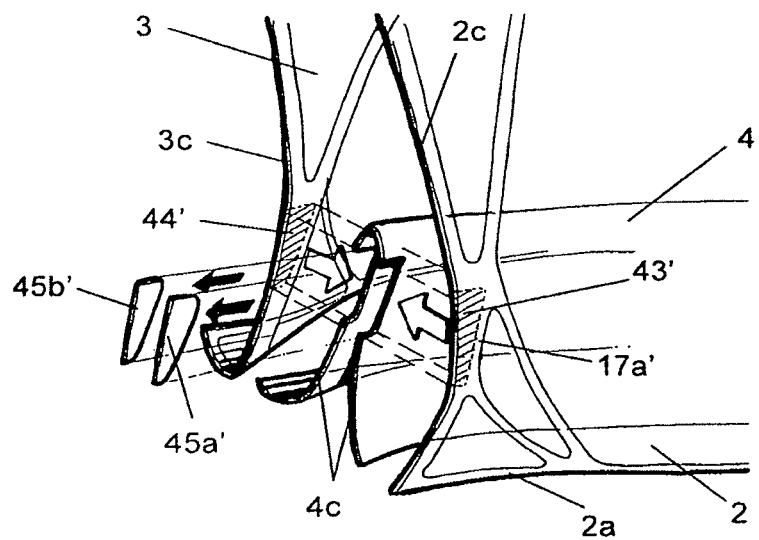

FIG. 3 shows the joining process of the two side wall sheets 2 and 3 and the bottom wall sheet 4 in detail. To increase the stability of the bag 1 it is useful to join the areas 43' and 44' of the two side wall sheets 2 and 3 between the fourth sloped sealing lines 17a', 17b' and the vertical edges 2c, 3c whereby the same applies to the other, not shown right hand side of the bag. Without any additional process step this would require to also join the corresponding parts of the bottom wall sheet 4, i.e. altogether four layers of elastomeric material would have to be welded together. Such welding procedures always bear the danger that a seal between any of the layers may be incomplete thus giving rise to increased instability and to forces that may damage other sealing lines and thus the integrity of the whole bag.

In the embodiment of the bag according to the invention that is shown in FIG. 3 the corresponding parts 45a' and 45b' of the bottom wall sheet 4 are therefore punched out from the bottom wall sheet 4 and removed before all sheets are joined as displayed in FIG. 3. Now a direct welding seal between the areas 43' and 44' of the two side wall sheets 2 and 3 can be established without any sandwiching layers from the bottom wall sheet 4.

Figure 4:
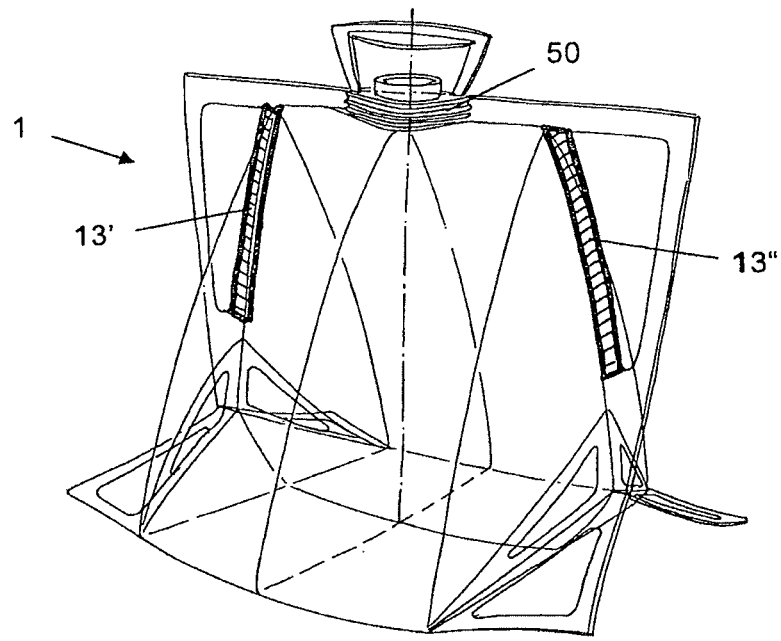

In order to avoid or minimise any damage of critical sealing lines in the case of the development of pressure waves in the liquid concentrate in the container should the bag be dropped accidentally, some of the sealing lines may at least partly consist of peel seams. In FIG. 4 the bag of FIG. 2 is shown wherein the first sloped sealing lines 13', 13" are made of such peelable seams. Should a pressure wave as a result of excessive pressure in the bag hit the various sealing lines of the bag the peel seams 13', 13" can partly or completely open, thereby absorbing and reducing the pressure and relieving the other sealing lines from a critical pressure condition.

Figure 5:
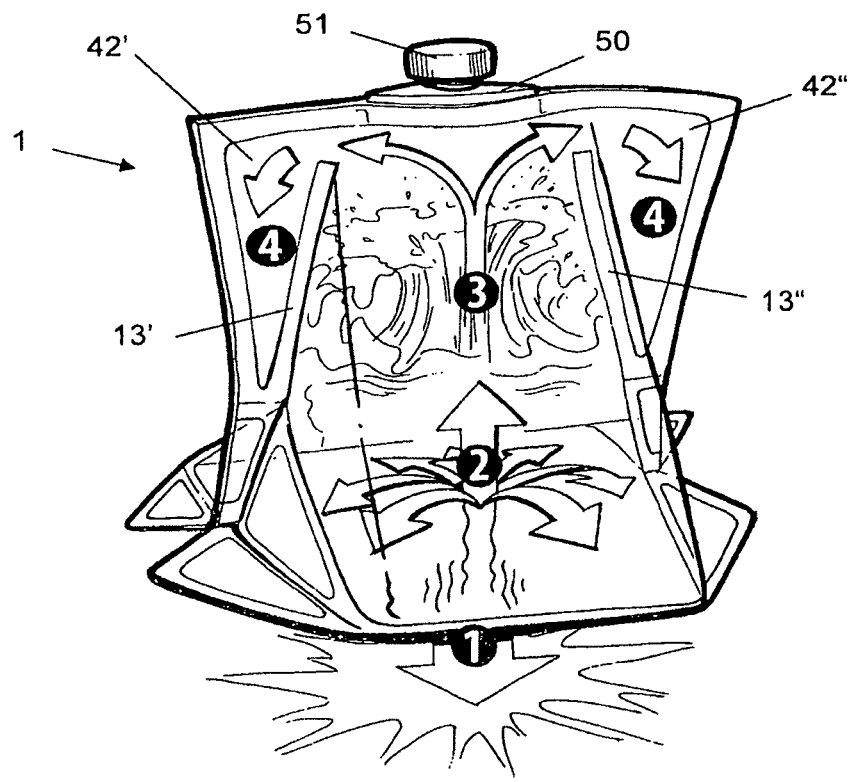

An alternative solution to absorb excessive pressure is provided in FIG. 5. In this embodiment the first sloped sealing lines 13', 13" are interrupted at the top of the bag. Should the bag be dropped (step 1) the pressure wave (step 2) expands into all directions and also to the air remaining at the top of the container (step 3), which further expands into the top side flap chambers 42',42" (step 4). As the total sealing line length is larger in this case as for the bag shown in FIG. 2 and as the air or liquid can also expand within the flexible flaps 42', 42" the pressure in the whole bag can significantly be reduced. As the first sloped sealing lines 13', 13" are only interrupted at a small length compared to their total length the stability of the bag 1 is not diminished.

With the aid of the bag according to the invention it is possible to provide 3 to 8 liters, preferably 5 to 6 liters of liquid dialysate concentrate in a self-standing bag made of elastomeric and flexible material sheets. The design of the bag guarantees that the bag remains in a stable upright position during use even when the bag contains less and lesser liquid at the end of a hemodialysis treatment.

Preferred geometries of the embodiment of a self-standing bag according to the invention as shown in the FIGS. 1 to 5 are provided in FIG. 6.

The self-standing bag 1 most conveniently contains a rigid connector part 50 as shown in FIGS. 2, 4 and 5. The connector part 50 has a wide middle part section and two tapered side wing parts to enable smooth transitions for the top sealing line 10. An orifice 53 in the wide middle part has a diameter large enough for a suction pipe of a dialysis device to reach into the interior of the bag. Any air tight sealing between the bag and the suction pipe is not necessary as in the case of conventional containers made of rigid material. The orifice 53 may comprise an inner, smaller orifice (not shown) as spill barrier.

The orifice can be closed after the bag has been filled by a tamper-proved lid 51 that may also be used to re-close the bag after use. The connector part 50 preferably comprises a handle 52 by which the whole bag can easily be carried. The handle 52 is linked to the main part of the connector 50 by suitable joints so that the handle 52 can be moved out of the way of the orifice 53 of the connector part 50 when a suction pipe is to be inserted into the bag.

Instead of a tamper-proved lid 51 a peelable disposable sheet may also be used to close the bag after filling, e.g. by appropriate heat sealing to the orifice 53. Such an embodiment is less costly and also provides a single-use indication as the sheet cannot be applied to the orifice again once it has been removed.

Figure 7:
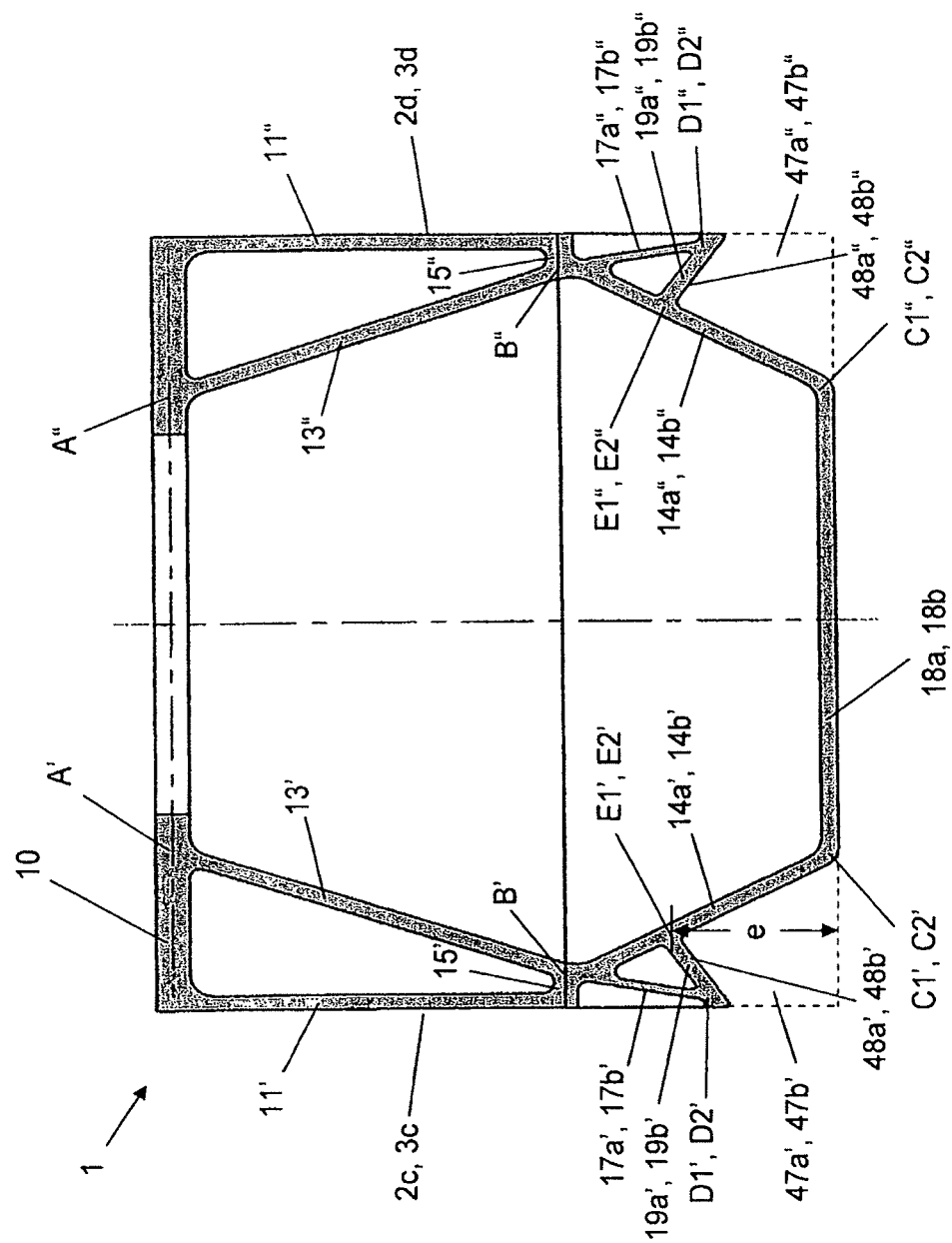

In FIG. 7 a second embodiment of the self-standing bag 1 according to the invention is shown in a view similar to that of FIG. 1a. The same reference numbers are used for identical parts of both embodiments of the bag. The cross-section as displayed in FIG. 1b is the same for the second embodiment which is why this view is omitted here.

As in the first embodiment the bag 1 shown in FIG. 7 also comprises the first sloped sealing lines 13', 13" between the first points A', A" and the second points B', B", the second sloped lines 14a', 14a" and 14b', 14b" between the second points B', B" and the third points C1', C1" and C2', C2" and the fourth sloped sealing lines 17a', 17a" and 17b', 17b" between the second points B', B" and the fourth points D1', D1" and D2', D2". However, the third sealing lines of the first embodiment are not present in the second embodiment. Instead the sheet material of the side wall sheets 2 and 3 and the bottom wall sheet 4 in the corner areas 47a', 47b' and 47a", 47b" below the fourth sloped sealing lines 17a', 17a" and 17b', 17b" and below cutting edges 48a', 48a" and 48b', 48b" leading from the fourth points D1', D1" and D2', D2" to fifth points E1', E1" and E2', E2" on the second sloped sealing lines 14a', 14a" and 14b', 14b" is removed, wherein the fifth points E1', E1" and E2', E2" are recessed from the horizontal bottom edges 2a, 3a of the side wall sheets by a fifth distance e. The removal of the sheet material may take place after, before or even during the sealing process of the bag.

The bag 1 may comprise fifth sloped sealing lines 19a', 19a" and 19b', 19b", preferably welding lines, on each side of the bag between the fourth and the fifth points joining only the bottom wall sheet 4 and the neighbouring side wall sheet 2; 3 directly at the cutting edges 48a', 48a" and 48b', 48b".

Figure 8:
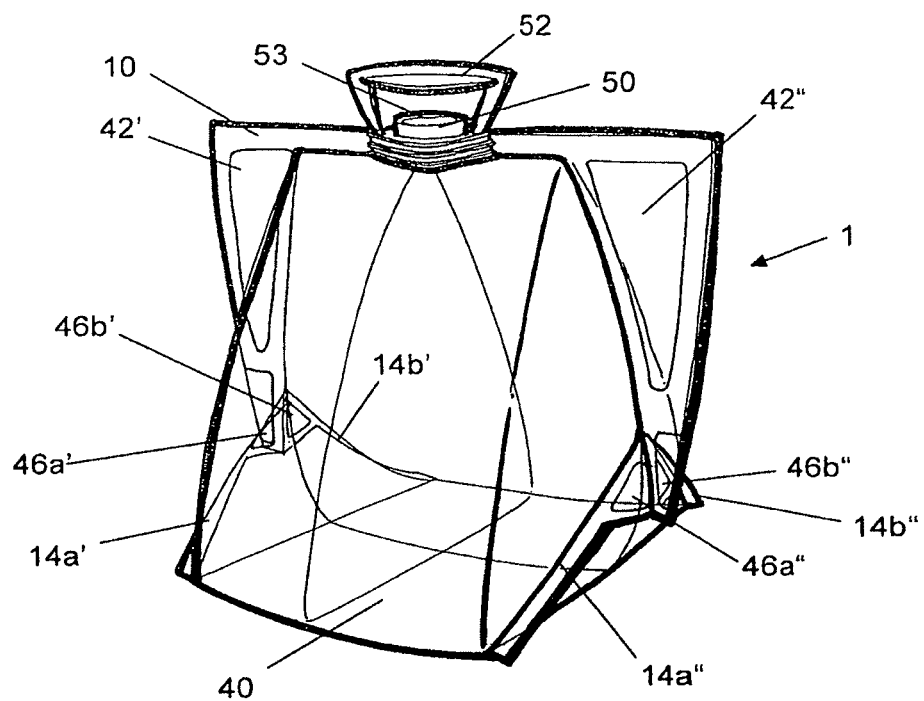

FIG. 8 shows the self-standing bag 1 according to the second embodiment of the invention in a three-dimensional configuration when being filled similar to the view of FIG. 2. For reasons of clarity the liquid itself is again not depicted. In this configuration the inner part of the self-standing bag 1 is similar for both embodiments which leads to a comparable position of the centre-of-gravity. The vertical stability is also enhanced by the top side flaps 42' and 42" and the sealing lines at their edges. However, the horizontal stability is achieved by the second sloped sealing lines 14a', 14b' and 14a", 14b" and the creation of beak-like flaps 46a', 46b' and 46a", 46b" on both sides of the filled bag 1. These beak-like flaps protect the zones around the second points B', B", where four sheets of the side wall sheets and the bottom wall sheet are joined, from any stress that results from the fluid inside the bag 1 statically and dynamically when the bag is moved or dropped. At the same time the flaps enhance the horizontal stability of the second sloped sealing lines as they provide a constraint between the second sloped sealing lines 14a', 14a" between the one side wall sheet 2 and the bottom wall sheet 4 and the corresponding second sloped sealing lines 14b', 14b" between the other side wall sheet 3 and the bottom wall sheet 4.

Figure 9:
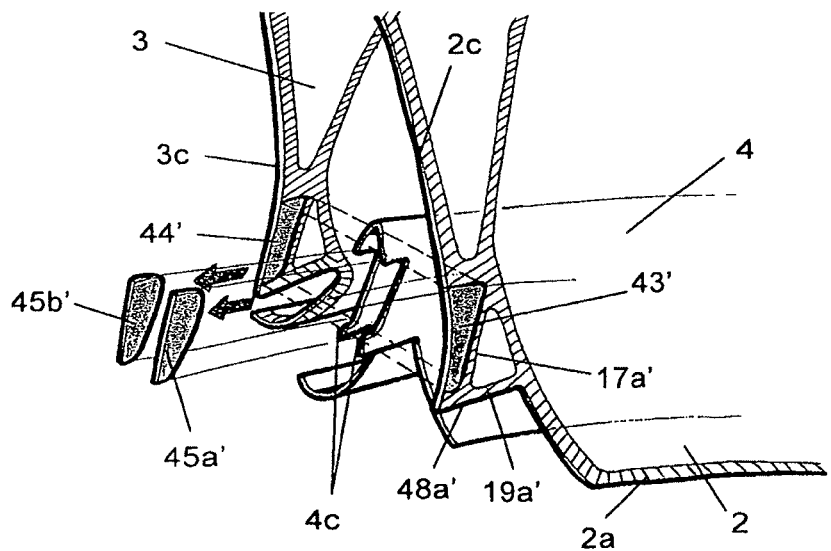

As depicted in FIG. 9 the joining of the bottom and side wall sheets of the bag can be realised for the second embodiment of the self-standing bag 1 similarly as in the case of the first embodiment. The description of FIG. 3 therefore applies mutatis mutandis to FIG. 9. Also the concepts as disclosed in FIGS. 4 and 5 can easily be combined with the design of the self-standing bag according to the second embodiment.

Preferred geometries of the second embodiment of the self-standing bag according to the invention are also compiled in the table of FIG. 6.

Figure 10:
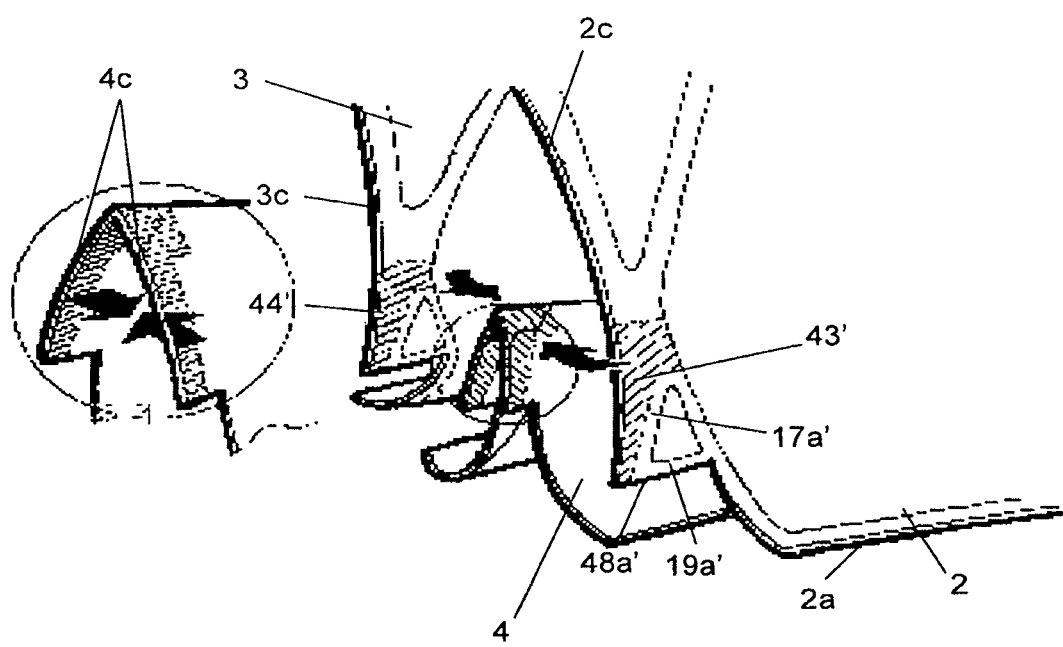

FIG. 10 shows an alternative for the joining of the bottom and side wall sheets according to a third embodiment of the self-standing bag according to the invention. The third embodiment is similar to the second embodiment but the parts 45a' and 45b' of the bottom wall sheet 4 are not punched out and removed before all sheets are joined. Instead a welding between the areas 43' and 44' of the two side wall sheets 2 and 3 together with the sandwiched folded layers from the bottom wall sheet 4 can be established. Without the modification according to the third embodiment described below it has turned out to be difficult to achieve a firm joining in this area of the bag during manufacture without negatively influencing any neighbouring welding lines.

In this embodiment at least the bottom wall sheet 4 has a layered structure consisting of at least two different outer layers. Both side wall sheets and the outer layer of the bottom wall sheet facing the side wall sheets during the welding process are preferably made from the same material. Using suitable materials for the sheets and layers it is possible to accomplish a tight and stable welding seal even though in fact four sheets are joined. The side wall sheets may have the same layered structure as the bottom wall sheet so that in this case all sheets can be made from the same material web. The other outer layer of the bottom wall sheet 4 which is at the surface of the folded bottom wall sheet where the folded parts of the bottom wall sheet face each other should preferably have a different, higher melting temperature than the first outer layer of the bottom wall sheet. As will become apparent in the example described below this has the advantage that the various welding steps can be conveniently separated.

The following combination of material layers has proven to be particularly advantageous. All three sheets 2, 3 and 4 have a first outer layer made of polyethylene (PE) and a second outer layer made of polypropylene (PP) or polyamide (PA). The side wall sheets 2 and 3 are arranged before welding so that their PE layers face each other. The bottom wall layer 4 is folded so that the PP or PA layers of the folded parts face each other. After having been inserted between the side wall sheets the PE layers of the folded bottom wall sheet face the PE layers of each side wall sheet. As the PP-PP or PA-PA welding requires higher melting temperatures compared with the PE-PE welding, both PE-PE welding zones (thick arrows in the right image of FIG. 10) can be created by using conventional welding tools to create the necessary temperature without simultaneously welding the PP-PP or PA-PA contact area, leaving the folded bottom wall sheet not sticking or welded to itself. The use of conventional welding tools enables in this case the formation of additional welding lines of the bag at the same time. In a subsequent process step it is then possible to locally heat up only the areas 43' and 44' again to then deliberately join the inner PP-PP or PA-PA surfaces (thick arrows in the left enlargement image of FIG. 10). The local melting of the PE-PE welds in these areas has no consequences as the welds are simply formed again, and the remainder of the PE-PE welds are not influenced at all.

Depending on the material suitable welding methods can be chosen for the inner welding. Examples are ultrasonic or thermal contact welding methods.

Using a layered structure in particular for the bottom wall sheet according to the third embodiment of the bag according to the invention to save the removal of sheet material is not limited to a variation of the second embodiment. It can also be utilised for the first embodiment or other variations of the bag according to the invention where four material sheets have to be joined.

The embodiments of self-standing bags as explicitly disclosed in this patent document provide for an superior rigidity even if masses of 3 kg and more have to be provided and transported. Such bags may also be used for other purposes than for the transport of liquid dialysate concentrate. Loads of preferably four to six bags can easily be grouped together in hard paper boxes that can be piled on palettes thus allowing for convenient shipping of the filled bags. If the bags are manufactured at a different place than where the bags are filled they can be left in a flat configuration that permits efficient and non-bulky piling. Such bags, independent of whether being filled or being empty, are therefore explicitly considered as being a part of the concept of the disclosed invention.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A self-standing bag filled with a liquid dialysate for making dialysate for a dialysis treatment comprising:

a self-standing bag made of two flexible elastomeric rectangular side wall sheets, each side wall sheet having horizontal top and bottom edges and two vertical edges, and one flexible elastomeric rectangular bottom wall sheet having two horizontal edges and two vertical edges;

said two rectangular side wall sheets being sealed to one another along their vertical edges in a lateral two-layer part of said bag;

the two vertical edges of said bottom wall sheet being sealed to adjacent vertical edge parts of said side wall sheets and said two horizontal edges of said bottom wall sheet being sealed to adjacent horizontal bottom edges of the side wall sheets in a lateral four-layer part of the bag, said sealing of the side wall sheets to each other and to the bottom wall sheet defining a maximum sealed volume of an interior of said bag;

the bag when empty capable of a flat configuration in which the bottom wall sheet is sandwiched between the two side wall sheets, the bottom wall sheet is symmetrically single-folded parallel to the bottom wall sheet horizontal edges, and the horizontal edges of the bottom wall sheet coincide with the horizontal bottom edges of the two side wall sheets, the bag when empty and in the flat configuration thus having a line separating said lateral four-layer part and said lateral two-layer part;

said bag further including first sloped sealing lines on each side of the bag joining the side wall sheets in the lateral two-layer part between first points (A', A") on the horizontal top edges of the side wall sheets, that are recessed by a first distance (a) from the sealed vertical edges of the side wall sheets, and second points (B', B") that are recessed by a second distance (b) from the sealed vertical edges of the side wall sheets and that are positioned on the line separating the lateral two-layer part from the lateral four-layer part, the second distance being less than the first distance, said first sloped sealing lines reducing the maximum sealed volume of said bag interior;

said bag still further including second sloped sealing lines joining each side wall sheet and the neighbouring bottom wall sheet in the lateral four-layer part on each side of the bag, between third points (C1', C1"; C2', C2") on the horizontal bottom edges of the side wall sheets, that are recessed by a third distance (c) from the sealed vertical edges of the side wall sheets and the second points (B', B"), said second sloped sealing lines further reducing the maximum sealed volume of said bag interior; and a liquid dialysate including 3 to 8 liters of an acidic part of liquid dialysate concentrate contained within said bag.

2. The self-standing bag according to claim 1, wherein a connector part is sandwiched between the two horizontal top edges, and the two horizontal top edges and the connector part are joined by a seal.

3. The self-standing bag according to claim 1, wherein the vertical edges of the side wall sheets are joined by seals in the lateral two-layer part.

4. The self-standing bag according to claim 1, wherein the vertical edges of the bottom wall sheet are joined with the neighbouring parts of the side wall sheets by seals.

5. The self-standing bag according to claim 1, wherein the horizontal edges of the bottom wall sheet are joined with the neighbouring horizontal bottom edges of the side wall sheets by seals.

6. The self-standing bag according to claim 1, wherein the side-wall sheets and the bottom wall sheet are made from a single web, and the horizontal bottom edges of the side wall sheets and the bottom wall sheet are made by folding the web along the horizontal edges.

7. The self-standing bag according to claim 1, wherein the second points (B', B") are recessed from the vertical edges of the side wall sheets and the bag further includes horizontal sealing lines between the second points (B', B") and the neighbouring vertical edges of the side wall sheets along the line separating the lateral two-layer part from the lateral four-layer part thus joining all four layers along the further horizontal sealing lines.

8. The self-standing bag according to claim 1, wherein the bag includes third sloped sealing lines or each side of the bag between the third points (C1', C1"; C2', C2") and fourth points (D1', D1"; D2', D2") on the vertical edges of both the side wall sheets and the bottom wall sheet in the lateral four-layer part joining only the bottom wall sheet and the neighbouring side wall sheet, the fourth points (D1', D1"; D2', D2") being recessed from the horizontal edges of the side wall sheets by a fourth distance (d).

9. The self-standing bag according to claim 8, wherein the bag includes fourth sloped sealing lines on each side of the bag between the second (B', B") and the fourth (D1', D1"; D2', D2") points joining only the bottom wall sheet and the neighbouring side wall sheet.

10. The self-standing bag according to claim 9, wherein the sheet material of the bottom wall sheet in the area between the fourth sloped sealing lines and the vertical edges has been removed on each side of the bag and both side wall sheets are directly joined in this area.

11. The self-standing bag according to claim 1, wherein the bag includes fourth sloped sealing lines on each side of the bag between the second points (B', B") and fourth points (D1', D1"; D2', D2") on the vertical edges of both the side wall sheets and the bottom wall sheet in the lateral four-layer part joining only the bottom wall sheet and the neighbouring side wall sheet, the fourth points (D1', D1"; D2', D2") being recessed from the horizontal edges of the side wall sheets by a fourth distance (d).

12. The self-standing bag according to claim 11, wherein the sheet material of the side wall sheets and the bottom wall sheet in the corner areas below the second sloped sealing lines and below cutting edges that lead from the fourth points (D1', D1"; D2', D2") to fifth points (E1', E1"; E2', E2") on the second sloped sealing lines is removed, the fifth points (E1', E1"; E2', E2") being recessed from the horizontal edges of the side wall sheets by a fifth distance (e).

13. The self-standing bag according to claim 12, wherein the bag includes fifth sloped sealing lines on each side of the bag between the fourth points (D1', D1"; D2', D2") and the fifth points (E1', E1"; E2', E2") joining only the bottom wall sheet and the neighbouring side wall sheet at the cutting edges.

14. The self-standing bag according to claim 11, wherein the sheet material of the bottom wall sheet in the area between the fourth sloped sealing lines and the vertical edges has been removed and both side wall sheets are directly joined in this area.

15. The self-standing bag according to claim 1, wherein the first sloped sealing lines are at least partly peel seams that are adapted to absorb excessive pressure in the bag.

16. The self-standing bag according to claim 1, wherein the first sloped sealing lines are at least partly interrupted providing a connection between the interior of the bag and top side flap chambers separated from the interior by the first sloped sealing lines.

17. The self-standing bag according to claim 1, wherein the bottom wall sheet is made of more than one layer and wherein a first outer layer and a second outer layer are made of different materials.

18. The self-standing bag according to claim 17, wherein one of the first outer layer and the second outer layer of the bottom wall sheet and one of the side wall sheets or at least a first outer layer and a second outer layer of the side wall sheets facing each other are made of the same material.

19. The self-standing bag according to claim 18, wherein the same material is polyethylene.

20. The self-standing bag according to claim 19, wherein the other outer layer of the bottom wall sheet is made of polypropylene or polyamide.

21. A self-standing bag filled with a liquid dialysate for making dialysate for a dialysis treatment, said self-standing bag made of two flexible elastomeric rectangular side wall sheets, each side wall sheet having horizontal top and bottom edges and two vertical edges, and one flexible elastomeric rectangular bottom wall sheet having two horizontal edges and two vertical edges;

said two rectangular side wall sheets being sealed to one another along their vertical edges in a lateral two-layer part of said bag;

the two vertical edges of said bottom wall sheet being sealed to adjacent vertical edge parts of said side wall sheets and said two horizontal edges of said bottom wall sheet being sealed to adjacent horizontal bottom edges of the side wall sheets in a lateral four-layer part of the bag, said sealing of the side wall sheets to each other and to the bottom wall sheet defining a maximum sealed volume of an interior of said bag;

the bag when empty capable of a flat configuration in which the bottom wall sheet is sandwiched between the two side wall sheets, the bottom wall sheet is symmetrically single-folded parallel to the bottom wall sheet horizontal edges, and the horizontal edges of the bottom wall sheet coincide with the horizontal bottom edges of the two side wall sheets, the bag when empty and in the flat configuration thus having a line separating said lateral four-layer part and said lateral two-layer part;

said bag further including first sloped sealing lines on each side of the bag joining the side wall sheets in the lateral two-layer part between first points (A', A") on the horizontal top edges of the side wall sheets, that are recessed by a first distance (a) from the sealed vertical edges of the side wall sheets, and second points (B', B") that are recessed by a second distance (b) from the sealed vertical edges of the side wall sheets and that are positioned on the line separating the lateral two-layer part from the lateral four-layer part, the second distance being less than the first distance, said first sloped sealing lines reducing the maximum sealed volume of said bag interior;

said bag still further including second sloped sealing lines joining each side wall sheet and the neighbouring bottom wall sheet in the lateral four-layer part on each side of the bag, between third points on the horizontal bottom edges of the side wall sheets, that are recessed by a third distance (c) from the sealed vertical edges of the side wall sheets and the second points (B', B"), said second sloped sealing lines further reducing the maximum sealed volume of said bag interior; and said bag yet further including horizontal sealing lines between the second points (B', B") and the neighbouring vertical edges of the side wall sheets along the line separating the lateral two-layer part from the lateral four-layer part, thus joining all four layers along the further horizontal sealing lines.

22. A self-standing bag filled with a liquid dialysate for making dialysate for a dialysis treatment, said self-standing bag made of two flexible elastomeric rectangular side wall sheets, each side wall sheet having horizontal top and bottom edges and two vertical edges, and one flexible elastomeric rectangular bottom wall sheet having two horizontal edges and two vertical edges, the bag when empty capable of a flat configuration in which the bottom wall sheet is sandwiched between the two side wall sheets, the bottom wall sheet is symmetrically single-folded parallel to the bottom wall sheet horizontal edges, and the horizontal edges of the bottom wall sheet coincide with the horizontal bottom edges of the two side wall sheets, the bag when empty and in the flat configuration thus having a line separating a lateral four-layer part and a lateral two-layer part;

said bag further including first sloped sealing lines on each side of the bag joining the side wall sheets in the lateral two-layer part between first points (A', A") on the horizontal top edges of the side wall sheets, that are recessed by a first distance (a) from the vertical edges of the side wall sheets and second points (B', B") that are recessed by a second distance (b) from the vertical edges of the side wall sheets and that are positioned on the line separating the lateral two-layer part from the lateral four-layer part, the second distance being less than the first distance;

said bag still further including second sloped sealing lines joining each side wall sheet and the neighbouring bottom wall sheet in the lateral four-layer part on each side of the bag, between third points on the horizontal bottom edges, that are recessed by a third distance (c) from the ends of the horizontal bottom edges of the side wall sheets, and the second points (B', B"); and said bag yet further including fourth sloped sealing lines on each side of the bag between the second points (B', B") and fourth points (D1', D1"; D2', D2") on the vertical edges of both the side wall sheets and the bottom wall sheet in the neighbouring side wall sheet, the fourth points (D1', D1"; D2", D2") being recessed from the horizontal bottom edges of the side wall sheets by a fourth distance (d).

23. The self-standing bag according to claim 22, wherein the sheet material of the side wall sheets and the bottom wall sheet in the corner areas below the second sloped sealing lines and below cutting edges that lead from the fourth points (D1', D1"; D2', D2") to fifth points (E1', E1"; E2', E2") on the second sloped sealing lines is removed, the fifth points (E1', E1"; E2', E2") being recessed from the horizontal bottom edges of the side wall sheets by a fifth distance (e).

24. The self-standing bag according to claim 23, wherein the bag includes fifth sloped sealing lines on each side of the bag between the fourth points (D1', D1"; D2', D2") and the fifth points (E1', E1"; E2', E2") joining only the bottom wall sheet and the neighbouring side wall sheet at the cutting edges.

25. The self-standing bag according to claim 22, wherein the sheet material of the bottom wall sheet in the area between the fourth sloped sealing lines and the vertical edges has been removed and both side wall sheets are directly joined in this area.

* * * * *